(12) United States Patent
Yasuda et al.

(10) Patent No.: US 9,539,366 B2
(45) Date of Patent: Jan. 10, 2017

(54) METHOD FOR INDUCING REGENERATION OF CARTILAGE

(75) Inventors: Kazunori Yasuda, Sapporo (JP); Yoshihito Osada, Sapporo (JP); Jian Ping Gong, Sapporo (JP); Nobuto Kitamura, Sapporo (JP)

(73) Assignee: National University Corporation Hokkaido University, Sapporo-Shi, Hokkaido (JP)

( * ) Notice: Subject to any disclaimer, the term of this patent is extended or adjusted under 35 U.S.C. 154(b) by 552 days.

(21) Appl. No.: 13/174,311

(22) Filed: Jun. 30, 2011

(65) Prior Publication Data

US 2011/0257763 A1 Oct. 20, 2011

Related U.S. Application Data

(62) Division of application No. 12/312,829, filed as application No. PCT/JP2007/001320 on Nov. 29, 2007, now abandoned.

(30) Foreign Application Priority Data

Nov. 29, 2006 (JP) ................................. 2006-321450

(51) Int. Cl.
*A61L 27/52* (2006.01)
(52) U.S. Cl.
CPC ............ *A61L 27/52* (2013.01); *A61L 2430/02* (2013.01)
(58) Field of Classification Search
CPC ............................ A61L 27/52; A61L 2430/02
See application file for complete search history.

(56) References Cited

U.S. PATENT DOCUMENTS

| 6,103,865 A | * | 8/2000 | Bae et al. | 528/373 |
| 6,140,452 A | * | 10/2000 | Felt et al. | 528/60 |
| 2005/0043814 A1 | * | 2/2005 | Kusanagi | A61F 2/30756 623/23.58 |
| 2005/0147685 A1 | * | 7/2005 | Osada et al. | 424/487 |
| 2006/0177387 A1 | * | 8/2006 | Slavin et al. | 424/50 |

FOREIGN PATENT DOCUMENTS

| JP | 2006-42795 | 2/2006 |
| JP | 2006-213868 | 8/2006 |
| WO | WO 98/52543 | 11/1998 |
| WO | WO 00/27358 A | 5/2000 |
| WO | WO 02/50143 A | 6/2002 |
| WO | WO 03/093337 | 11/2003 |
| WO | WO 2006/001313 | 1/2006 |
| WO | WO 2006/013612 | 2/2006 |

OTHER PUBLICATIONS

Shastri et al "Osteocompatibility of Photopolymerizable Anhydride Networks," Mat. Res. Soc. Symp. Proc. vol. 530, 93-98, 1998).*
V.R. Shastri et al., "Osteocompability of Photopolymerizable Anhydride Networks", Materials Research Society Symposium Proceedings, 1998, pp. 93-98, vol. 530.
Susan L. Riley et al., "Formulation of PEG-Based Hydrogels Affects Tissue-Engineered . . . ", Journal of Materials Science: Materials in Medicine, 2001, pp. 983-990, vol. 12.
Jian Ping Gong et al., "Double-Network Hydrogels with Extremely High Mechanical Strength", Advance Materials, 2003, pp. 1155-1158, vol. 15.
Jun Kumagai et al., "Immunohistochemical Distributions of Type I, II and III Collagens in the Rabbit Supraspinatus Tendon Insertion", 1994, pp. 279-284, vol. 185.
Biomaterials. 25(9):1523-32, abstract (2004).

* cited by examiner

*Primary Examiner* — Suzanne Ziska
(74) *Attorney, Agent, or Firm* — RatnerPrestia

(57) ABSTRACT

It is intended to provide a medical material which enables a new method for cartilage tissue regeneration treatment based on an entirely new concept unlike a treatment method by transplantation of autologous cartilage tissue, a cartilage alternative or undifferentiated cells. The invention provides a bone filler for cartilage tissue regeneration comprising hydrogel having an interpenetrating network structure formed by two or more crosslinked network polymers or a semi-interpenetrating network structure formed by a crosslinked network polymer and a linear polymer. By filling the bone filler of the invention in a hole or a groove provided in subchondral bone just under damaged cartilage tissue, regeneration of the cartilage tissue or both the cartilage tissue and the subchondral bone can be promoted.

3 Claims, 17 Drawing Sheets
(14 of 17 Drawing Sheet(s) Filed in Color)

METHOD FOR INDUCING REGENERATION OF CARTILAGE

This is a 37 CFR §1.53(b) divisional application of application Ser. No. 12/312,829 of May 28, 2009 now abandoned which was filed under 35 U.S.C. 371 based on the PCT International Application No. PCT/JP2007/001320 of Nov. 29, 2007, which is hereby incorporated in its entirety by reference.

TECHNICAL FIELD

The present invention relates to a bone filler useful in cartilage tissue regeneration treatment in a joint tissue.

BACKGROUND OF THE ART

A joint tissue, such as knee joint or shoulder joint tissue in particular, is covered with a cartilage tissue at the top of bones which are linked by a joint so as to prevent direct friction therebetween. Damage of the cartilage tissue due to aging, enormous or repeated loads thereon will cause inflammation in a joint, resulting in arthralgia on a patient. In fact, damaged joint cartilage tissue and arthralgia are highly frequently found in both young and aged patients. In order to improve their quality of life (QOL) and even provide more effective treatment in view of medical economics, development of effective and efficient joint treatment method is increasingly required.

In the treatment of damaged cartilage tissue, the most major problem is to find out a method for regenerating such a cartilage tissue, which is difficult to naturally regenerate in vivo by drug administration, etc. For example, microfracture method that generates numerous microholes on a subchondral bone forms a fibrocartilage, but no hyaline cartilage as a normal articular cartilage is regenerated. Consequently, a damaged cartilage tissue is normally treated by transplanting an in vivo cartilage tissue.

Joint treatment methods by transplanting an in vivo cartilage tissue are generally classified into 2 types: autologous osteochondral transplantation method (Mosaicplasty) and cultured autologous chondrocytes transplantation (implantation) method. The autologous osteochondral transplantation method (Mosaicplasty) harvests an autologous cartilage tissue from a normal part of damaged joint or a joint tissue opposite thereto using a bone plug and transplants it to a defect portion. However, this treatment method involves one inevitable problem, i.e., damage of a normal cartilage adjacent to a defect cartilage harvested, and another problem of insufficient amount of a cartilage portion to be transplanted from a significantly damaged cartilage tissue in vivo. Meanwhile, the method harvests part of an autologous cartilage (hyaline cartilage) tissue in a patient and cultures it on an appropriate medium and/or a culture substrate to regenerate the cartilage tissue in a test tube and transplant it to an affected area. The cultured autologous chondrocytes transplantation method poses various problems: preparation of extremely expensive facilities required for aseptic culture of cartilage tissue, need for both harvesting and transplantation of cartilage tissue, higher treatment costs due to a long duration of patient's hospitalization, zoonotic risk due to contamination from culture process and unreliable treatment effects.

In order to avoid these problems, the development of a treatment method for promoting natural regeneration of cartilage tissue in vivo is of crucial importance. Current experimental methods include local administration of cytokines such as b-FGF and OP-1 to a joint containing damaged cartilage tissue in addition to a carrier, and administration of autogenous mesenchymal stem cell and ES cell to a joint containing damaged cartilage tissue. However, due to insufficiently known medical effects and problems like side effects, these methods are not served as practical application.

DISCLOSURE OF THE INVENTION

The present invention provides a medical material which enables a new method for in vivo cartilage tissue natural regeneration treatment based on an entirely new concept unlike a treatment method by transplantation of autologous cartilage tissue, a cartilage alternative or undifferentiated cells.

The inventors found that hydrogel, comprising polymers having a crosslinked network structure, is usable as a bone filler for cartilage tissue regeneration treatment by special surgical treatment and completed each of the following inventions.

(1) A bone filler for cartilage tissue regeneration treatment, comprising hydrogel having an interpenetrating network structure formed by two or more polymers having a crosslinked network structure or a semi-interpenetrating network structure formed by a polymer having a crosslinked network structure and a linear polymer.

(2) The bone filler according to item (1), wherein a polymer having a crosslinked network structure or a linear polymer is a polymer consisting of a charged unsaturated monomer and/or an electrically neutral unsaturated monomer.

(3) The bone filler according to item (2), wherein a charged unsaturated monomer is an unsaturated monomer having acidic group and/or basic group.

(4) The bone filler according to item (3), wherein acidic group is carboxyl group, phosphate group, sulfonic acid group or salt consisting thereof.

(5) The bone filler according to item (3), wherein an unsaturated monomer having acidic group is 2-acrylamide-2-methylpropanesulfonic acid or salt consisting thereof.

(6) The bone filler according to item (2), wherein an electrically neutral unsaturated monomer is N,N-dimethylacrylamide.

(7) The bone filler for cartilage tissue regeneration treatment according to item (1), comprising hydrogel having an interpenetrating network structure comprising a polymer having a crosslinked network structure with 2-acrylamide-2-methylpropanesulfonic acid as a monomer and a polymer having a crosslinked network structure with N,N-dimethylacrylamide as a raw monomer.

A cartilage or cartilage tissue regeneration inducer, comprising hydrogel having an interpenetrating network structure formed by two or more polymers having a crosslinked network structure or a semi-interpenetrating network structure formed by a polymer having a crosslinked network structure and a linear polymer.

The cartilage or cartilage tissue regeneration inducer according to item (8), comprising hydrogel having an interpenetrating network structure comprising a polymer having a crosslinked network structure with 2-acrylamide-2-methylpropanesulfonic acid as a monomer and a polymer having a crosslinked network structure with N,N-dimethyl-acrylamide, acrylamide or 2-acrylamide-2-methylpropane sodium sulphate as a raw monomer.

By filling a bone filler of this invention in a hole or a groove provided in subchondral bone just under damaged cartilage tissue, regeneration of a cartilage tissue or both the cartilage tissue and the subchondral bone can be promoted. Such a treatment method can be significantly effective, because it is free from the above problems found in conventional autologous osteochondral transplantation and cultured autologous chondrocytes transplantation (implantation) methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects of this invention will be seen by reference to the description taken in connection with the drawings, in which.

BEST MODE FOR CARRYING OUT THE INVENTION

Figure 1:
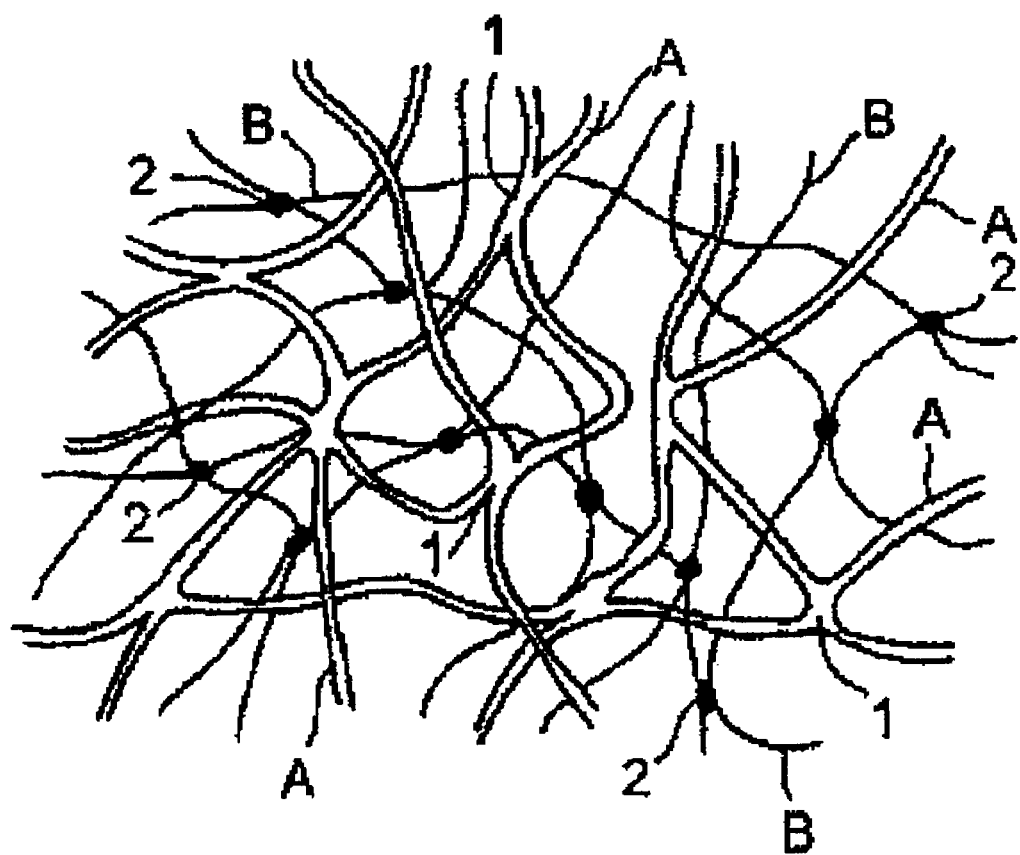
FIG. 1 is a schematic view indicative of "interpenetrating network structure" (double-network type) of this invention. A denotes a crosslinked network polymer, B denotes another crosslinked network polymer, and numerals 1 and 2 denote crosslink points of crosslinked network polymers A and B, respectively. This figure is a conceptual diagram of a gel containing a solvent (water) in a network structure.

A bone filler of this invention comprises hydrogel having an interpenetrating network structure formed by two or more polymers having a crosslinked network structure (polymer having a crosslinked network structure is hereinafter called crosslinked network polymer) or a semi-interpenetrating network structure formed by a crosslinked network polymer and a linear polymer. The crosslinked network structure of this invention, as shown in e.g., FIG. 1 of WO2006/013612 (shown as FIG. 1 in this specification), is a network structure formed by polymers having a plurality of crosslink points. Likewise, "interpenetrating network structure" of this invention means that two or more crosslinked network polymers are intertwined so as to interpenetrate in network structures with each other, resulting in a formation or state that internally includes a plurality of network structures. As shown in FIG. 1, the "interpenetrating network structure" is composed of a crosslinked network polymers A having a plurality of crosslink points 1 and a crosslinked network polymer B having a plurality of crosslink points 2, thereby presenting a formation or state in which both crosslinked network polymers A and B interpenetrate in network structures with each other and are physically intertwined.

"Semi-interpenetrating network structure" of this invention means that a linear polymer is intertwined in a crosslinked network polymer so as to interpenetrate therein, resulting in a formation or state of hydrogel that internally includes a plurality of network structures. As shown in e.g., FIG. 2 of WO2006/013612 (shown as FIG. 2 in this specification), the "semi-interpenetrating network structure" comprises a crosslinked network polymer C having a plurality of crosslink points 3 and a linear polymer D, thereby presenting a formation or state of hydrogel in which the linear polymer D interpenetrates in the crosslinked network polymer C and they are physically intertwined.

A hydrogel having "interpenetrating network structure" of this invention may include the above semi-interpenetrating network structure in which a linear polymer is partially intertwined, and "semi-interpenetrating network structure" of this invention may include "interpenetrating network structure" in which another crosslinked network polymer is partially intertwined. Specifically, one hydrogel may concurrently have an interpenetrating network structure and a semi-interpenetrating network structure.

Figure 2:
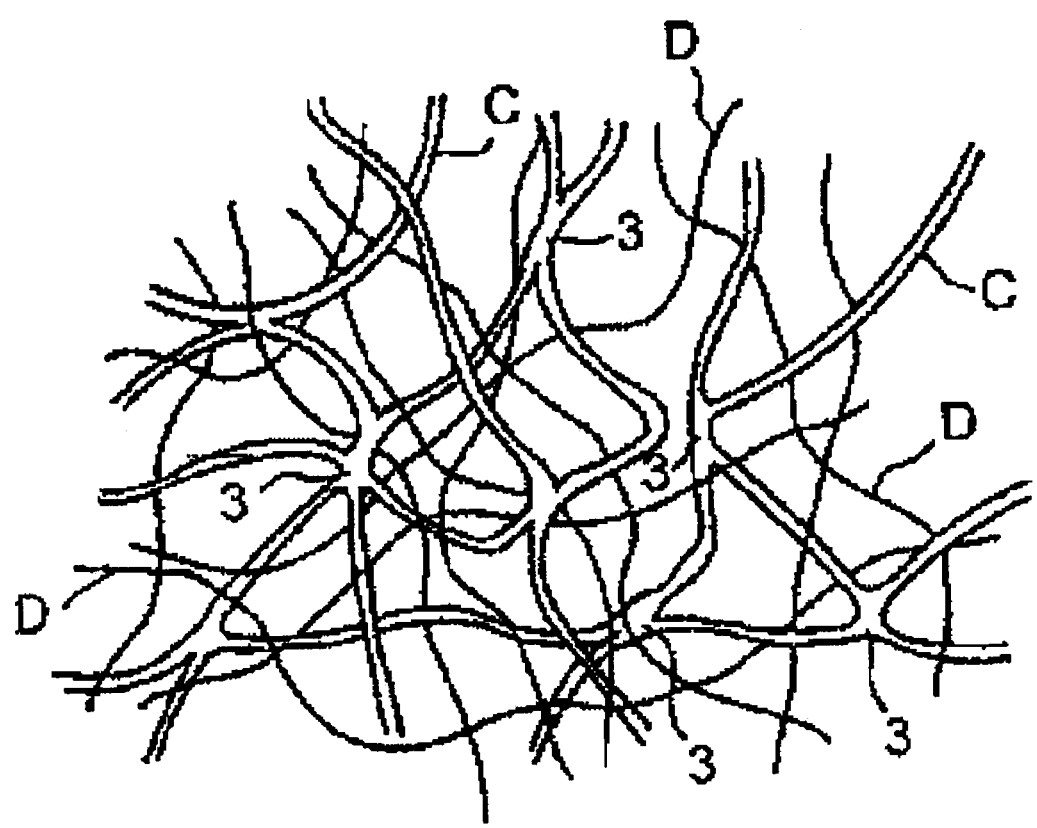
FIG. 2 is a schematic view indicative of "semi-interpenetrating network structure" (double-network type) of this invention. C denotes a crosslinked network polymer, D denotes a linear polymer, and a numeral 3 denotes a crosslink point of the crosslinked network polymer C.

In FIGS. 1 and 2, first network structures A and C are drawn by a thicker line than a second network structure B and a linear polymer D for the sake of convenience. Conceptually, "interpenetrating network structure" and "semi-interpenetrating network structure" each include a structure consisting of not only two polymers (double-network type) but also three or more polymers. "Two or more polymers" means that there exist two or more polymers forming "interpenetrating network structure" or "semi-interpenetrating network structure." In this definition, two or more polymers can be different or same as chemical substances that form a network structure.

In this invention, two or more polymers comprising an interpenetrating network structure are preferably a combination of polymers consisting of an unsaturated monomer having a positively/negatively chargeable group and polymers consisting of an unsaturated monomer having an electrically neutral group. The unsaturated monomer having a positively/negatively chargeable group is preferably an unsaturated monomer having acidic group (e.g. carboxyl group, phosphate group and sulfonic acid group) or basic group (e.g. amino group), for example, 2-acrylamide-2-methylpropanesulfonic acid (AMPS), acrylic acid (AA), methacrylic acid or salt consisting thereof. Also, the unsaturated monomer having an electrically neutral group can be, for example, dimethylsiloxane, styrene (St), acrylamide (AAm), N-isopropylacrylamide, N,N-dimethyl-acrylamide, vinylpyridine, styrene, methylmethacrylate (MMA), fluoride-containing unsaturated monomer (e.g. trifluoroethylacrylate (TFE)), hydroxyethyl acrylate or vinyl acetate.

In case of hydrogel usable in this invention, unsaturated monomers having a positively/negatively chargeable group are polymerized to form a first network structure beforehand. After including the unsaturated monomers having an electrically neutral group in this network portion, the unsaturated monomers having an electrically neutral group are polymerized or polymerized/crosslinked to form "interpenetrating network structure" or "semi-interpenetrating network structure." In both "interpenetrating network structure" and "semi-interpenetrating network structure," the degree of crosslinking for a crosslinked network polymer can be set at any value in the range of approx. 0.1 to 20 mole % in a first crosslinked network and approx. 0 to 20 mole % in a second crosslinked network, preferably approx. 0.5 to 10 mole % in a first crosslinked network and approx. 0 to 5 mole % in a second crosslinked network, more preferably approx. 2 to 6 mole % in a first crosslinked network and approx. 0 to 2 mole % in a second crosslinked network. Here, the "degree of crosslinking" is a percentage rate, a proportion of molar concentration of crosslinking agent to charged molar concentration of monomer. The degree of crosslinking for two or more crosslinked network polymers in "interpenetrating network structure" can be each set separately. For example, the degree of crosslinking for a crosslinked network polymer having a positively/negatively chargeable group may be set at a larger or smaller value than the degree of crosslinking for a crosslinked network polymer having an electrically neutral group. A crosslinking agent may be used in accordance with monomer component.

A hydrogel usable in this invention and production methods thereof are disclosed in detail in e.g., WO2003/093337, WO2006/013612, Japanese Unexamined Patent Application Publication No. 2006-042795, WO2006/001313, Japanese Unexamined Patent Application Publication No. 2006/213868, and Advanced Materials (J. P. Gong et al., Vol. 15, pp 1155-1158, 2003), etc, all of which are relevant to this invention by the inventors. In this invention, the gels described in all of these prior publications can be used. A bone filler of this invention doesn't specify mechanical intensity required for artificial semilunar cartilage disclosed in e.g., WO2006/013612. Thus, a hydrogel of this invention and production methods thereof doesn't always require various conditions for improving the intensity of hydrogel described herein.

A preferred bone filler of this invention is hydrogel having an interpenetrating network structure comprising a crosslinked network polymer with 2-acrylamide-2-methylpropanesulfonic acid (AMPS) as a raw monomer (PAMPS) and a crosslinked network polymer with N,N-dimethyl-acrylamide (DMAA) as a raw monomer (PDMAAm) (hereinafter called PAMPS/PDMAAm gel). PAMPS/PDMAAm gel is produced according to a method as described in Example 23 of WO2006/013612. The PAMPS/PDMAAm gel has a coefficient of friction of about $10^{-3}$, which is almost equivalent to that of a cartilage, and its physical properties show almost no change in a 6-week subcutaneous implantation test. In a pellet implantation test, an inflammatory reaction after 1 week is significantly stronger than a negative control and significantly weaker than a positive control, but the inflammatory reaction becomes weaker than the negative control 4 and 6 weeks later.

Meanwhile, both hydrogel having an interpenetrating network structure comprising a crosslinked network polymer with 2-acrylamide-2-methylpropanesulfonic acid (AMPS) as a raw monomer (PAMPS) and a crosslinked network polymer with acrylamide as a raw monomer (PAAm) (hereinafter called PAMPS/PAAm gel), and another hydrogel having an interpenetrating network structure comprising a crosslinked network polymer with 2-acrylamide-2-methylpropane sodium sulphate (Sodium 2-acrylamido-2-methylpropanesulfate, NaAMPS) as a raw monomer (PNaAMPS) and a crosslinked network polymer with N,N-dimethyl-acrylamide (DMAA) as a raw monomer (PDMAAm) (hereinafter called PNaAMPS/PDMAAm gel) have a function of promoting cartilage tissue regeneration, as well as the PAMPS/PDMAAm gel.

A bone filler of this invention requires an intensity which is not so high as an artificial cartilage, but in view of operability in filling in a bone and an ability to promote cartilage tissue regeneration, the intensity preferably reaches a certain level. For example, a mechanical intensity of PAMPS/PDMAAm gel and PAMPS/PAAm gel as the above preferred embodiment can be given as follows.

TABLE 1

|  | PAMPS/PAAm gel | PAMPS/PDMAAm gel |
|---|---|---|
| Tangent Modulus (MPa) | 0.3 (0.05) | 0.20 (0.01) |
| Ultimate Stress (MPa) | 11.40 (2.60) | 3.10 (0.29) |
| Strain at Failure (mm/mm) | 0.83 (0.05) | 0.73 (0.01) |
| Water Content (%) | 90.90 (0.3) | 94.00 (0.00) |

Next, a method for using a bone filler according to the present invention will be described.

Figure 13:
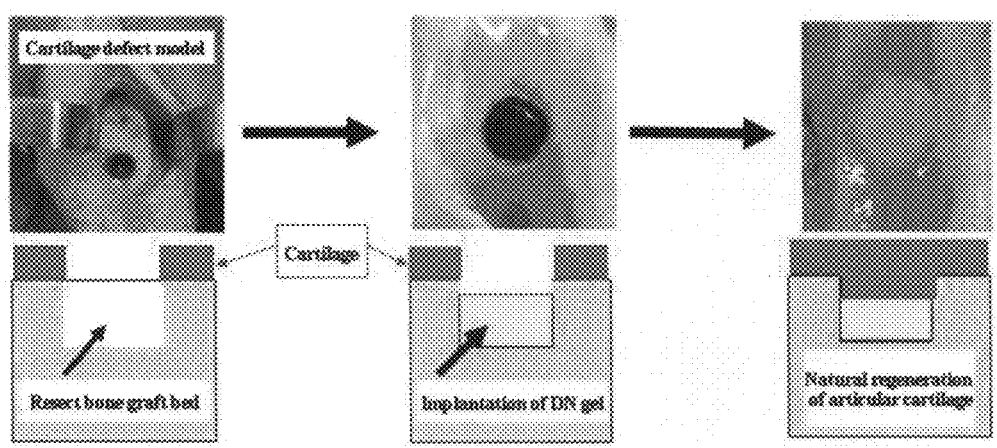
FIG. 13 is a schematic view of cartilage regeneration treatment using a bone filler of this invention.

The bone filler according to the present invention is used in surgical treatment, aimed at cartilage tissue regeneration. This surgical treatment resects a subchondral bone just below a damaged cartilage tissue in addition thereto to provide a hole or a groove having an appropriate depth therein (hereinafter called bone defect portion), in which the bone filler of this invention is filled so as to leave a bone defect portion having an appropriate depth. FIG. 13 schematically shows the above surgical treatment using the bone filler of this invention.

As a conventionally existing therapeutic concept, artificial cartilage cannot ensure cartilage regeneration. In fact, this alternative artificial material is connected with a cartilage surface to be filled to leave no bone defect, and the method thereof is completely different from a method for using an artificial material in this invention. Using the bone filler of this invention, the cartilage tissue regeneration by surgical treatment is an unprecedented method, because it is not necessary to transplant a cartilage tissue harvested in vivo and administer a special liquid factor that promotes cartilage regeneration. Specifically, this natural regeneration process can be achieved by providing biological and dynamic environment therefor by filling a gel material in the subchondral bone. In addition to cartilage tissue regeneration, subchondral bone tissue regeneration can be performed in a manner that the bone filler filled in the bone defect portion is covered, and cartilage tissue regeneration can be subsequently achieved so that regenerated subchondral bone tissue is covered. With an unprecedentedly surprising result, the bone filler of this invention can not only regenerate a cartilage tissue in vivo, which is conventionally believed impossible, but also the subchondral bone as well.

The surgical treatment using the bone filler of this invention, as described above, resects a subchondral bone just below a damaged cartilage tissue in addition thereto to provide a bone defect portion, in which the bone filler of this invention is filled so as to leave a bone defect portion having an appropriate depth. The surgical treatment can preferably determine a filling volume of hydrogel so that there exists a distance between an articular surface of a cartilage tissue on the periphery of the bone defect portion (defined as a surface opposite to the surface bordering the subchondral bone, simply called articular surface) and a surface of hydrogel facing the articular surface (hereinafter called surface of hydrogel). In case of Japanese white rabbits to be shown in Example, a distance between an articular surface of bone defect portion and a surface of hydrogel is 5 mm or less, preferably 0.7 to 2.8 mm, and more preferably 0.7 to 2.1 mm. The distance is preferably set according to subject biological species and dynamic environment on the periphery of a cartilage area.

The bone filler of this invention is non-toxic to living organisms in that it is used by filling in a bone, and it is not always necessary to remove the filler from the bone defect portion after a cartilage tissue or both of the cartilage tissue and a subchondral bone tissue have been regenerated. Thus, a patient can receive a surgical treatment using the bone filler of this invention only once, in which the bone filler is filled by providing a bone defect portion, thereby reducing physical and psychological burdens on a patient unlike conventional methods requiring several treatments.

Since the bone filler of this invention can induce regeneration of a subchondral bone tissue and a cartilage tissue regeneration by placing it in a bone defect portion as described above, this invention is intended to be in use with said hydrogel as a cartilage and/or cartilage tissue regeneration inducer, or as a cartilage and/or cartilage tissue regeneration accelerator.

Examples of production and use of the bone filler of this invention will be shown to describe this invention in more detail, but these examples are not particularly limited to this invention.

EXAMPLE

Example 1

A silicone frame (80 mm in length, 80 mm in width, 5 mm in thickness and 5 mm in frame width) was prepared and a side thereof was provided with a 3 mm internally directed groove. The silicone frame was sandwiched between 2 glass plates (100 mm in length, 100 mm in width and 3 mm in thickness) to prepare a polymerization vessel.

25 mL of 2 mol/L 2-acrylamide-2-methylpropanesulfonic acid (AMPS) aqueous solution, 1 mL of 2 mol/L N,N'-methylenebisacrylamide (MBAA) aqueous solution as a crosslinking agent, 0.5 mL of 0.1 mol/L 2-oxoglutarate aqueous solution and water were mixed to prepare 50 mL of aqueous solution. After the aqueous solution was deoxidized using nitrogen gas and fed into the groove of said polymerization vessel and the groove was sealed, PAMPS gel with a degree of crosslinking of 4 mol % (first network structure) was prepared by irradiating the deoxidized aqueous solution with ultraviolet rays at room temperature for 6 hours, using UV lamp (22 W, 0.34 A) with a wavelength of 365 nm, to cause polymerization reaction.

Next, 100 mL of 6 mol/L N,N-dimethyl-acrylamide (DMAA) aqueous solution, 2 mL of 0.1 mol/L N,N'-methylenebisacrylamide (MBAA) aqueous solution, 2 mL of 0.1 mol/L potassium persulfate aqueous solution and water were mixed to obtain 200 mL of aqueous solution (immersion solution). The immersion solution was deoxidized for 30 minutes using nitrogen gas.

Said PAMPS gel taken out from the polymerization vessel was immersed in the immersion solution that was moved to an appropriate bat and the gel was subjected to occasional gently shaking in the refrigerator at 4° C. for 2 days to diffuse and immerse said immersion solution in said PAMPS gel.

Subsequently, the gel was taken out from said immersion liquid and cut into pieces with a proper size. Afterward, the gel was sandwiched between 2 glass plates (100 mm in length, 100 mm in width and 3 mm in thickness) so as to include no foam therebetween. After sealing 4 sides on the edge of the 2 glass plates, DMAA was polymerized in a 60° C. water bath for 6 hours to produce a bone filler as hydrogel of double-network type (PAMPS/PDMAAm gel).

<Test 1>

Using a bone filler of this invention produced in Example, surgical treatment for cartilage tissue regeneration was performed as follows.

20 mature Japanese white rabbits (3.0 to 4.2 kg) were provided with a vertical bone defect portion (4.3 mm in diameter and 9.0 mm in depth) on femurs of both patell-ofemoral joint to fill PAMPS/PDMAAm gel (4.5 mm in diameter and 9.0 mm in length) produced in Example into a bone defect of the right knee by press-fitting. A distance between an articular surface of the bone defect portion and PAMPS/PDMAAm gel surface was set at 0.0 to 5.0 mm to fill the PAMPS/PDMAAm gel. Here, a distance of 0.0 mm means a state in which the PAMPS/PDMAAm gel is filled so that the articular surface and the PAMPS/PDMAAm gel surface yield a complete match, or a treatment group pertinent thereto. A distance of 5.0 mm means a state in which the PAMPS/PDMAAm gel is filled so that there is provided a gap of 5.0 mm between the articular surface and the PAMPS/PDMAAm gel surface, or a treatment group pertinent thereto.

After rearing the Japanese white rabbits in a cage for 4 weeks postoperatively and slaughtering them, their knee joints were visually observed and defect progress in the right and left knees were evaluated histologically (safranin-O staining: Hirotani et al., Rinsho-seikei-geka (Clinical Orthopedics), Vol. 11, No. 12, pp 40-44, 1976). In this histologic evaluation, femur section was prepared on a sagittal plane passing though the center of a circular damaged portion, and patella section was prepared on a midsagittal plane. The distance between an articular surface of the bone defect portion and the PAMPS/PDMAAm gel surface was measured at three points: a central portion of filled PAMPS/PDMAAm gel and 2 end points of the hydrogel positioned oppositely viewed from the central portion. Mean measured distance was defined as a distance between the articular surface of the bone defect portion and the PAMPS/PDMAAm gel surface. The 20 mature Japanese white rabbits (3.0 to 4.2 kg) were also provided with a vertical bone defect portion (4.3 mm in diameter, and 1 mm, 2 mm, 3 mm, 4 mm and 5 mm in depth randomly determined) on femurs of both knees/femur of patella. A group whose rabbits were kept in a cage for 4 weeks with nothing being filled was defined as untreated control group.

As a result, the untreated control group showed that the bone defect portion of any depth was filled with a new bone in most knees. Also, its superficial layer was covered with a fibrous tissue with a step left therein, and no cartilage tissue was confirmed. Some knees demonstrated a mixture of a fibrous tissue and a fibrochondroid tissue on a superficial layer of the new bone, but no regeneration of a hyaline cartilage cell.

Meanwhile, a group in which PAMPS/PDMAAm gel produced in Example was filled in the bone defect portion showed the following results according to a distance between an articular surface and PAMPS/PDMAAm gel surface.

Figure 3:
FIG. 3 shows a histologic stained image (safranin-O stained image) when the distance between an articular surface of bone defect portion and a surface of hydrogel having an interpenetrating network structure comprising a polymer having a crosslinked network structure with 2-acrylamide-2-methylpropanesulfonic acid as a monomer and a polymer having a crosslinked network structure with N,N-dimethyl-acrylamide as a raw monomer (hereinafter called PAMPS/PDMAAm gel) is 0.0 mm. The pink-color stained part shows a cartilage tissue.

1) Distance of 0.0 mm (FIG. 3)

No specific change was observed on the periphery of the bone defect portion, compared with the untreated control group, and hydrarthrosis was not found. The state of the bone defect portion which was filled with PAMPS/PDMAAm remained unchanged. A bony wall by a new bone was found so as to surround the border between the PAMPS/PDMAAm gel and the bone defect portion, and a cartilage tissue was regenerated partially thereon.

Figure 4:
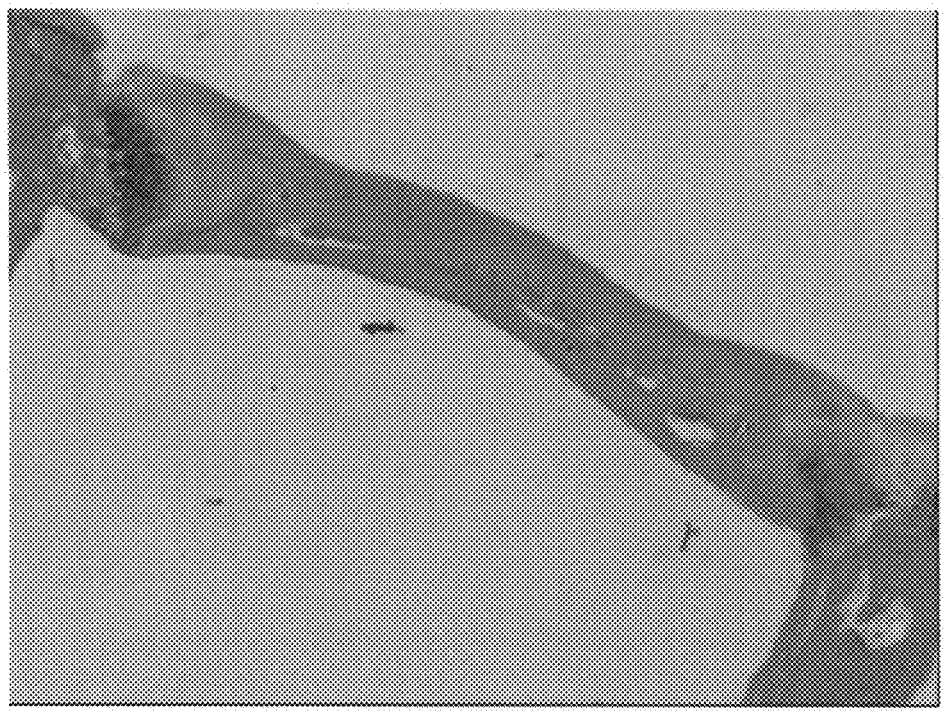
FIG. 4 shows a histologic stained image (safranin-O stained image) when the distance between an articular surface of bone defect portion and PAMPS/PDMAAm gel surface is 0.0 mm to 0.6 mm. A pink-color stained part shows a cartilage tissue.

2) Distance of 0.0 mm to 0.6 mm (FIG. 4)

The PAMPS/PDMAAm gel surface was covered with a thin fibrous tissue, and a chondroid tissue was found on the border between the PAMPS/PDMAAm gel and the bone defect portion.

Figure 5:
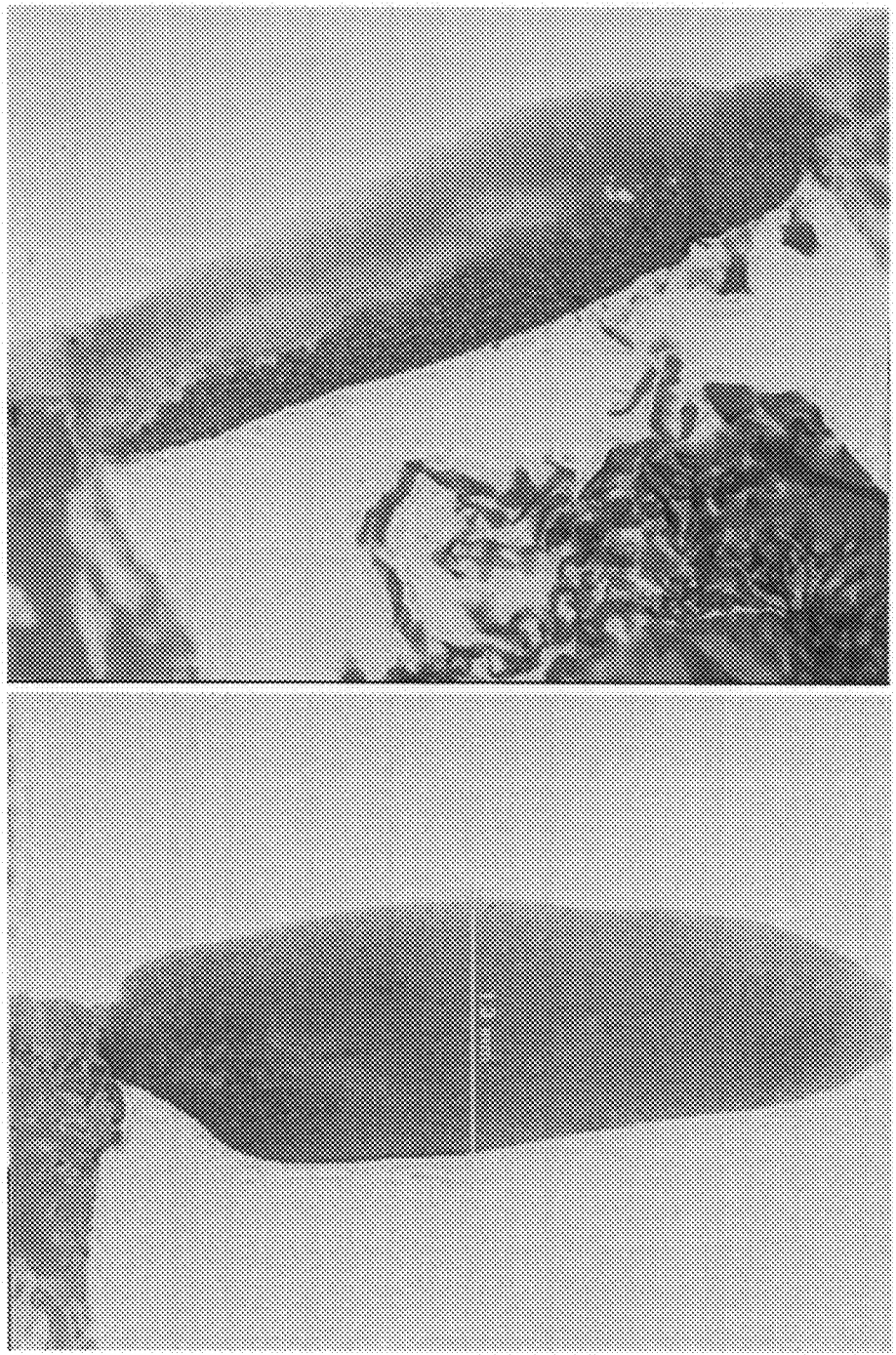
FIG. 5 shows histologic stained images (safranin-O stained image) when the distance between an articular surface of bone defect portion and PAMPS/PDMAAm gel surface is 0.7 mm to 1.3 mm. A pink-color stained part shows a cartilage tissue. Two photos each show a stained image of different individual cartilages with the same treatment condition.

3) Distance of 0.7 to 1.3 mm (FIG. 5)

The gap provided on PAMPS/PDMAAm gel surface was fully filled with a regenerated cartilage tissue. The regenerated cartilage tissue was sufficiently stained with safranin-O. The cartilage cell was found densely in the vicinity of the PAMPS/PDMAAm gel surface and thinly in the vicinity of the articular surface, with a normal cartilage-like distribution. The outermost layer of the regenerated cartilage tissue showed Lamina splendens-like structure.

Figure 6:
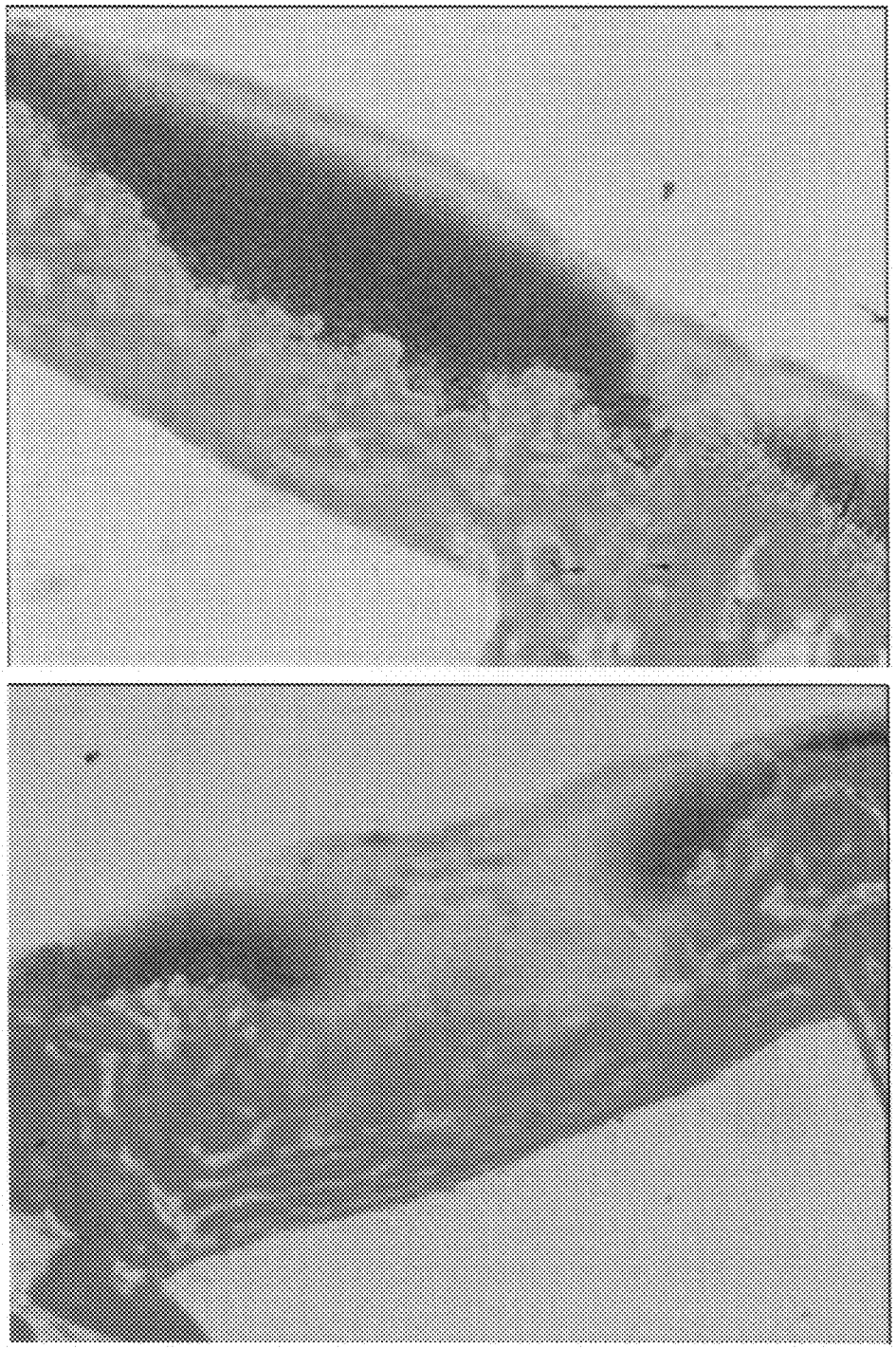
FIG. 6 shows histologic stained images (safranin-O stained image) when the distance between an articular surface of bone defect portion and PAMPS/PDMAAm gel surface is 1.4 mm to 2.0 mm. A pink-color stained part shows a cartilage tissue. Two photos each show a stained image of different individual cartilages with the same treatment condition.

4) Distance of 1.4 to 2.0 mm (FIG. 6)

Like the case in 3), the gap provided on PAMPS/PDMAAm gel surface was fully filled with a regenerated cartilage tissue. Subchondral bone neoplasticity was found between the PAMPS/PDMAAm gel surface and the regenerated cartilage tissue.

Figure 7:
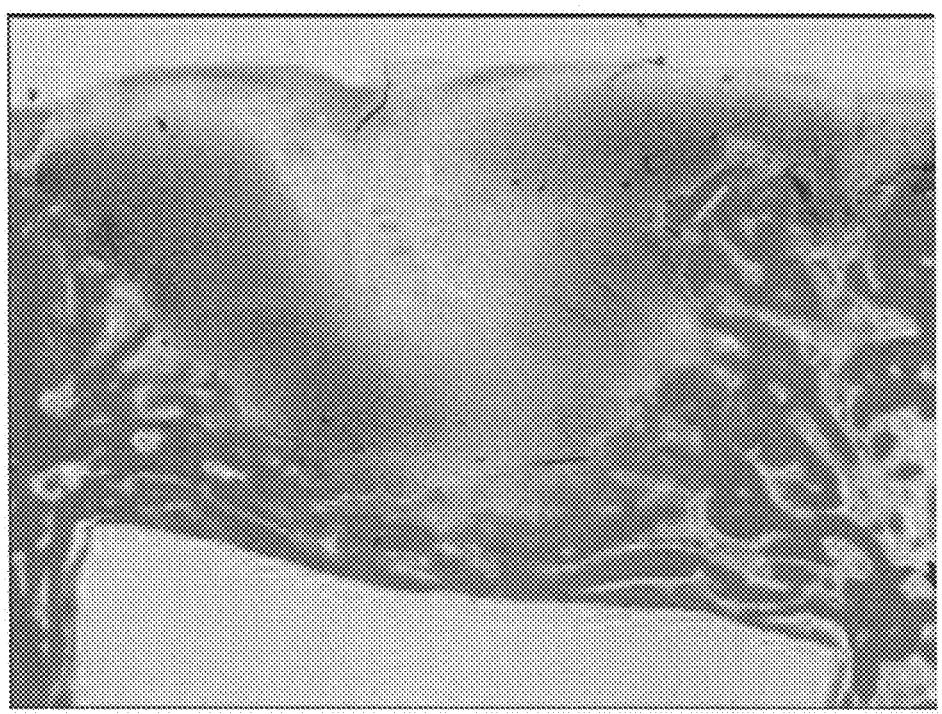
FIG. 7 shows a histologic stained image (safranin-O stained image) when the distance between an articular surface of bone defect portion and PAMPS/PDMAAm gel surface is 2.1 mm to 2.8 mm. A pink-color stained part shows a cartilage tissue.

5) Distance of 2.1 to 2.8 mm (FIG. 7)

The PAMPS/PDMAAm gel surface showed subchondral bone neoplasticity on which a cartilage tissue was regenerated. In the vicinity of the articular surface of regenerated cartilage tissue, a chondroid tissue composed of a mixture of a fibrous tissue and a cartilage tissue was regenerated. The chondroid tissue showed a thin new bone distribution therein.

Figure 8:
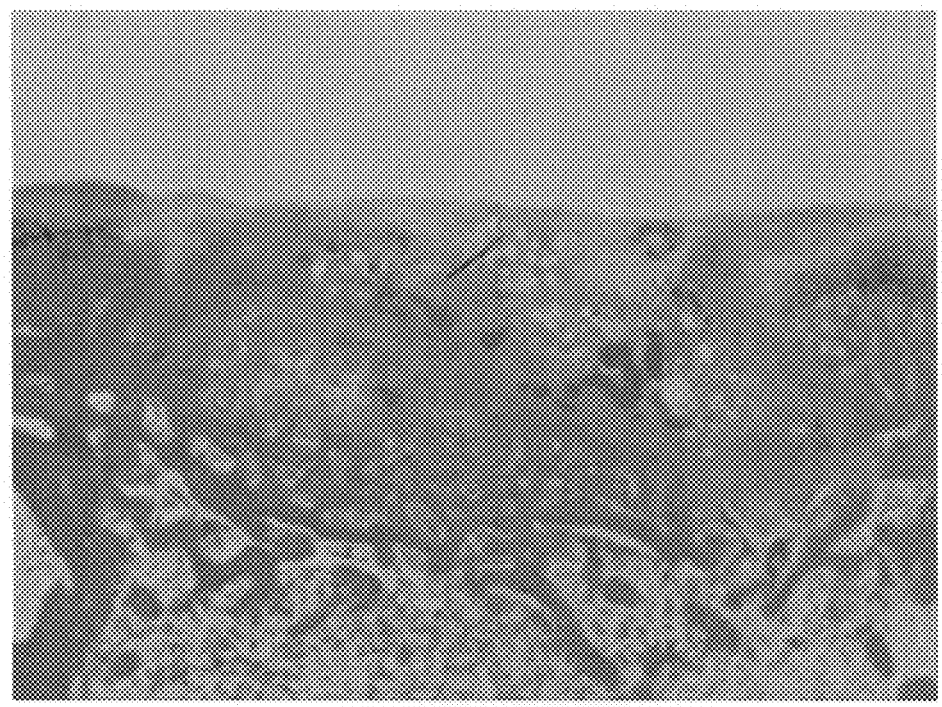
FIG. 8 shows a histologic stained image (safranin-O stained image) when the distance between an articular surface of bone defect portion and PAMPS/PDMAAm gel surface is over 2.8 mm. A pink-color stained part shows a cartilage tissue.

6) Distance of over 2.8 mm (FIG. 8)

The finding was similar to the untreated control group. The gap provided on the PAMPS/PDMAAm gel surface was filled with a new bone, and its surface portion was covered with a fibrous tissue with a step left therein. No cartilage tissue regeneration was confirmed. Some knees showed a mixture of a fibrous tissue and a fibrochondroid tissue on the surface of a new bone, but sequence structure of a cartilage cell was not found. Some knees presented internal ossification of a fibrochondroid tissue.

<Test 2>

Figure 14:
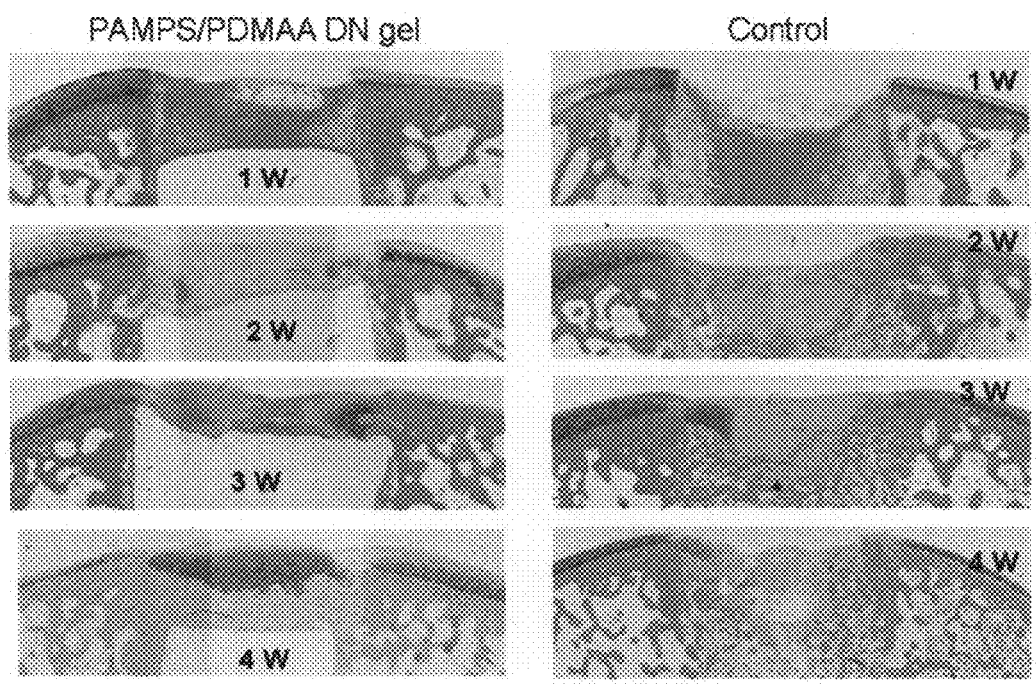
FIG. 14 shows histologic stained images (safranin-O stained image) indicative of changes according to elapsed time for 1 to 4 weeks when the distance between an articular surface of bone defect portion of Example 1 4) and PAMPS/PDMAAm gel surface is 1.4 mm to 2.0 mm.

Using specimen on which a distance in 4) of Test 1 was set at 1.4 to 2.0 mm, experiments were repeatedly performed to confirm cartilage tissue regeneration by safranin-O staining by 1 week. FIG. 14 shows the results.

<Test 3>

Figure 15:
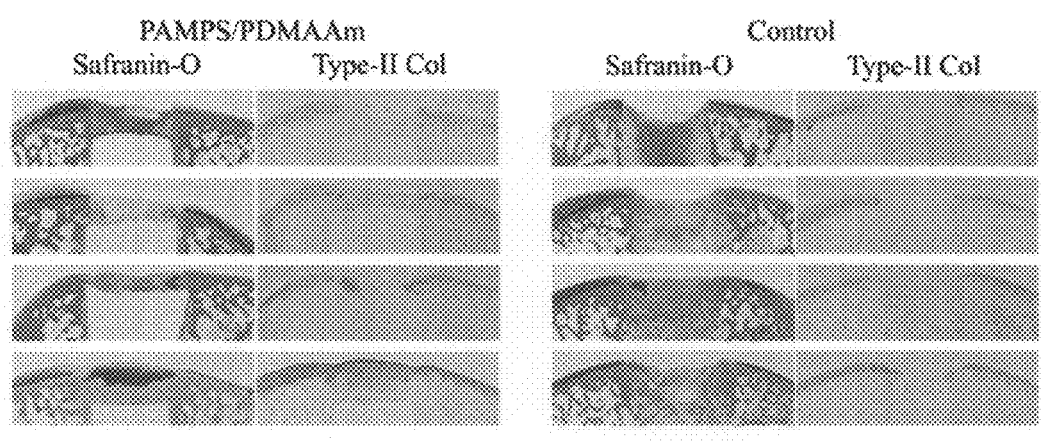
FIG. 15 shows immunohistological stained images of Type-II collagen at a regeneration site when the distance between an articular surface of bone defect portion of Example 1 4) and PAMPS/PDMAAm gel surface is 1.4 mm to 2.0 mm.

The expression of Type-II collagen at a regeneration site of the specimen in Test 2 was confirmed with reference to the method by Kumagai et al. (Kumagai et al., J. Anat., Vol. 185, pp 279-284, 1994). Specifically, a section was digested with ProteinaseK at room temperature for 6 minutes and then washed with PBS, and immersed in 1% hydrogen peroxide/methanol for 30 minutes. After the product was washed with PBS, it was incubated at room temperature for 60 minutes using 50-time diluted primary antibody (mouse anti-human collagen Type II antibody, Fuji Chemicals Industrial Co., Ltd.). Afterward, the product was rewashed with PBS and incubated at room temperature for 30 minutes using second antibody (anti-mouse IgG antibody, Envision). The color of the product was developed with DAB DAKO (DAB substrate set) and a nucleus was stained with hematoxylin. FIG. 15 shows its stained images.

<Test 4>

Tissues were harvested from a regeneration site of Test 2 and a site on the periphery of a treated portion after a control test, to extract RNA using RiboPure Kit (Ambion). 1 µg of RNA was subjected to reverse transcription reaction (at 37° C. for 15 minutes, and then at 85° C. for 5 seconds), using PrimeScriptRT™ Reagent Kit (TAKARA) to synthesize single-strand cDNA. In addition, mRNA volumes of 3 proteins (Type-II collagen, Aggrican and SOX9) known as a cartilage cell marker were analyzed by using primer DNA which was designed based on base sequence information on nucleic acid encoding each protein by Thermal Cycler Dice Real Time System Software. In this analysis, real-time PCR (40 cycles at 95° C. for 5 seconds and 60° C. for 30 seconds) was performed in Thermal Cycler Dice (registered trademark) TP800 (Takara), using SYBR (registered trademark) Premix Ex Taq (Takara). Base sequences of primer DNA were GCTACGACGCCATCTGCTAC (forward) and GTCTGGACCGTGATGTCCTC (reverse) in Aggrican, GACCATCAATGGCGGCTTC (forward) and CACGCTGTTCTTGCAGTGGTAG (reverse) in Type-II collagen, and AACGCCGAGCTCAGCAAGA (forward) and TGGTACTTGTAGTCCGGGTGGTC (reverse) in SOX9.

Figure 16:
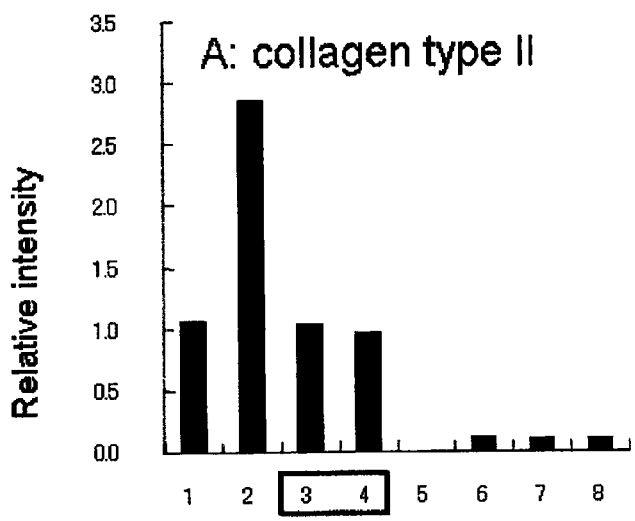
FIG. 16 shows graphs indicative of an mRNA volume of a cartilage tissue cell at a regeneration site of Test 2 for Type-II collagen (panel A) Aggrican (panel B) and SOX9 (panel C). Lanes 1 and 2 denote normal cartilage (positive control), lanes 3 and 4 denote specimen in which a filler of this invention is filled, lanes 5 and 6 denote specimen in which nothing is filled in bone defect portion, and lanes 7 and 8 denote specimen in which Ultra High Molecular Weight polyethylene (hereinafter called UHMPE) is filled in bone defect portion.
Figure 16:
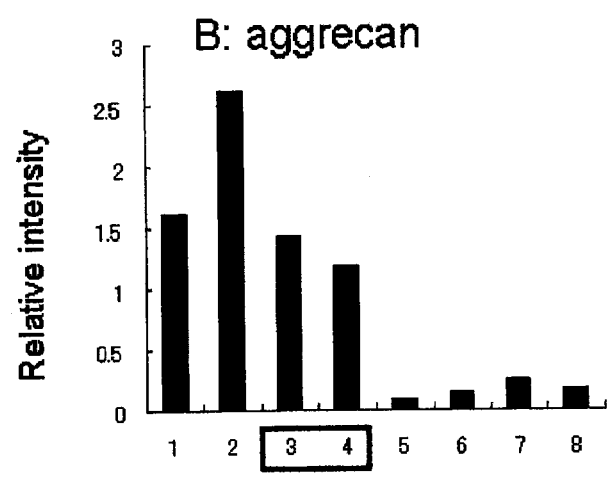
Figure 16:
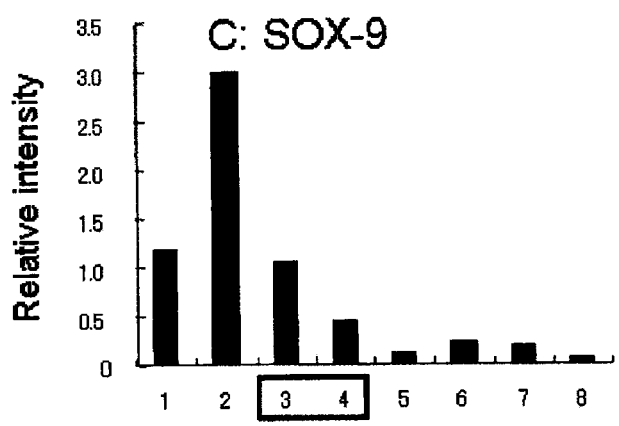

FIG. 16 shows the results. In a tissue with cartilage tissue regeneration found, the expression of mRNA in the above three marker proteins was confirmed. On the other hand, the control group showed almost no expression of all the marker proteins.

Example 2

The procedures were identical to Example 1, other than a use of acrylamide (AAm) having the same mole (6 mol/L) as N,N-dimethyl-acrylamide (DMAA), to produce a bone filler as hydrogel of double-network type (PAMPS/PAAm gel).

<Test 5>
Using the bone filler of this invention produced in Example 2, surgical treatment for cartilage tissue regeneration was performed using the same method as in Test 1. The group, in which PAMPS/PAAm gel produced in Example 2 was filled in the bone defect portion, showed the following results by a distance between an articular surface and PAMPS/PAAm gel surface.

Figure 9:
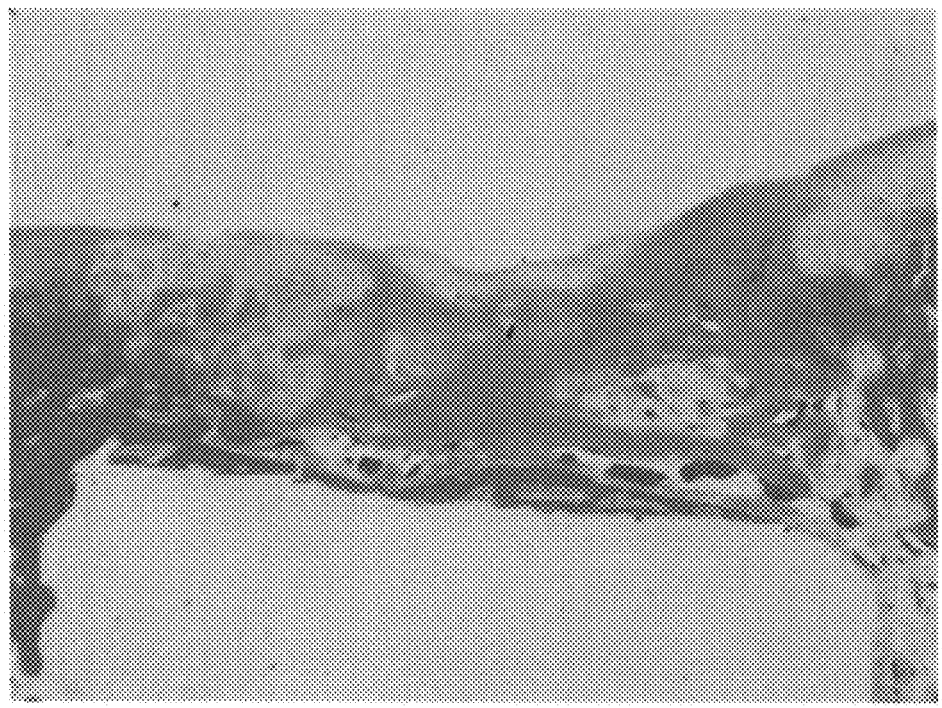
FIG. 9 shows a histologic stained image (safranin-O stained image) when the distance between an articular surface of bone defect portion and PAMPS/PAAm gel surface is 0.7 mm to 1.3 mm. A pink-color stained part shows a cartilage tissue.
Figure 10:
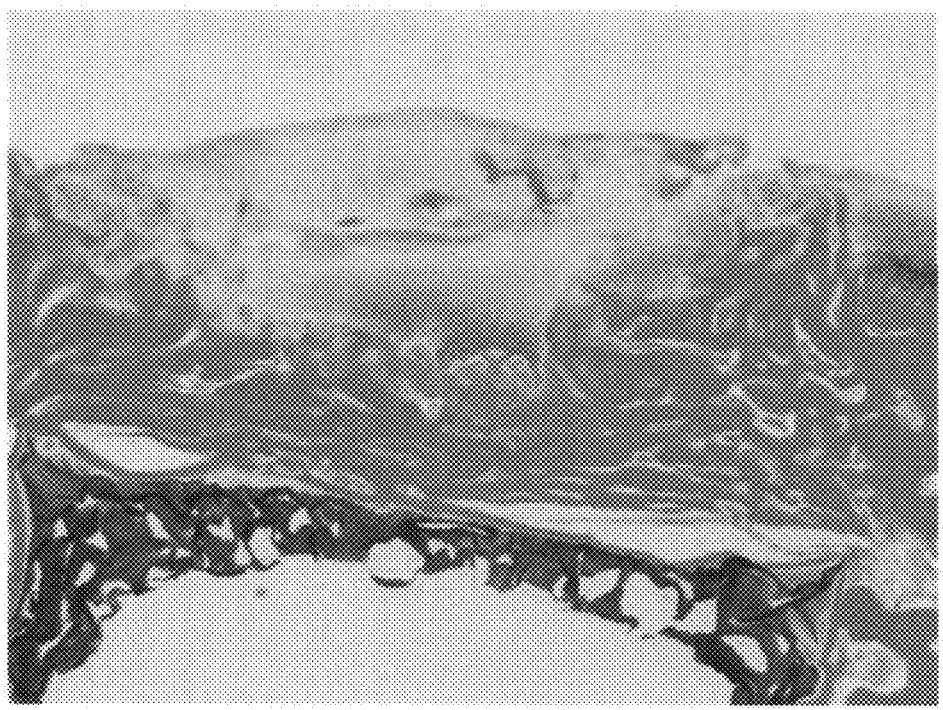
FIG. 10 shows a histologic stained image (safranin-O stained image) when the distance between an articular surface of bone defect portion and PAMPS/PAAm gel surface is 1.4 mm to 2.0 mm. A pink-color stained part shows a cartilage tissue.
Figure 11:
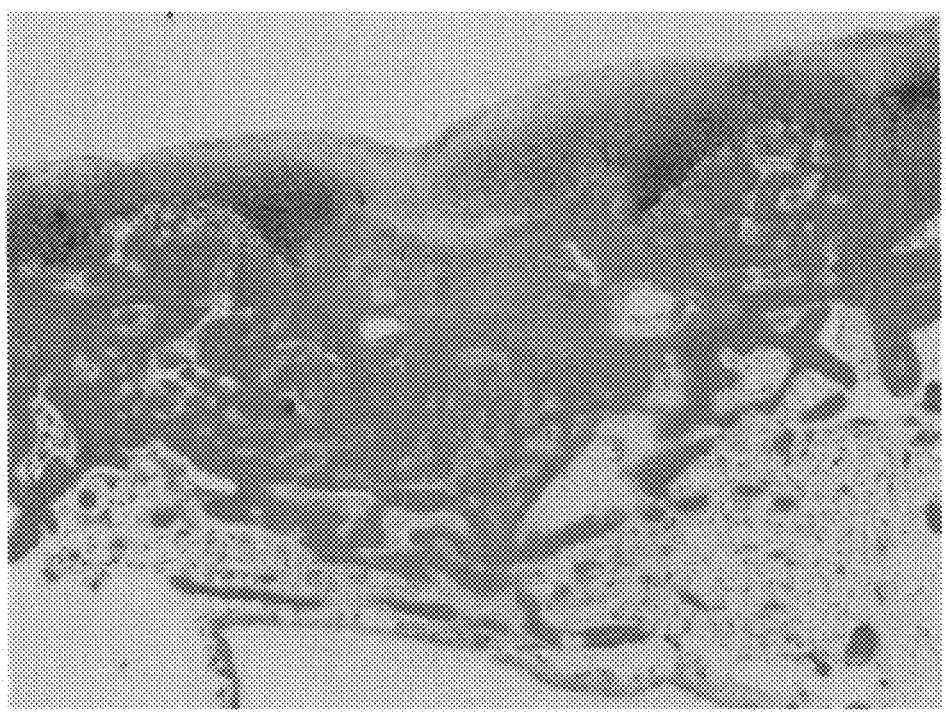
FIG. 11 shows a histologic stained image (safranin-O stained image) when the distance between an articular surface of bone defect portion and PAMPS/PAAm gel surface is 2.1 mm to 2.7 mm. A pink-color stained part shows a cartilage tissue.
Figure 12:
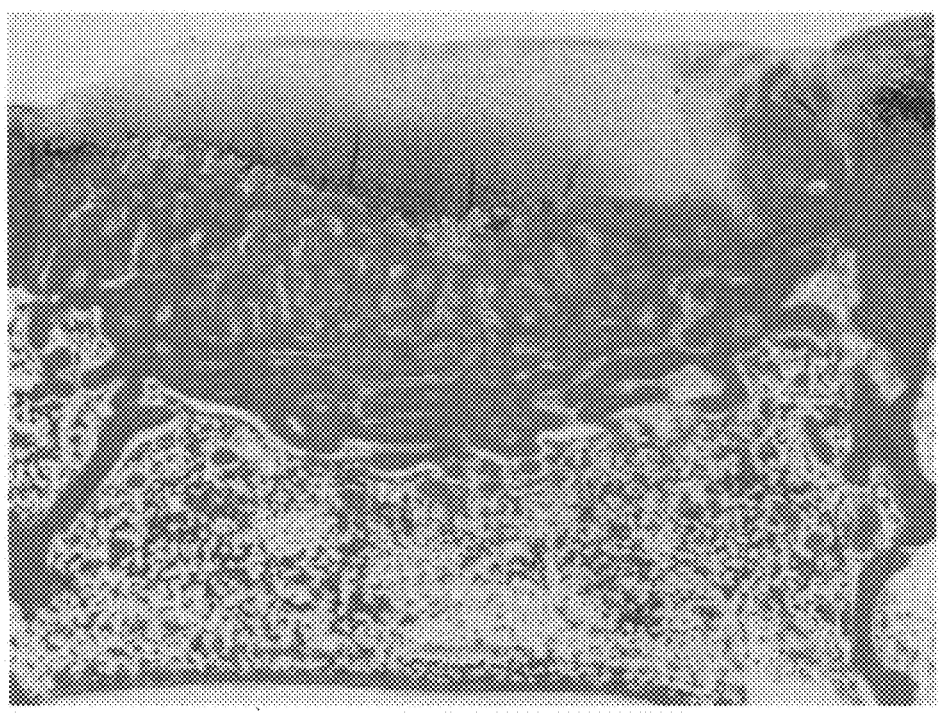
FIG. 12 shows a histologic stained image (safranin-O stained image) when the distance between an articular surface of bone defect portion and PAMPS/PAAm gel surface is over 2.8 mm. A pink-color stained part shows a cartilage tissue.

1) Distance of 0.0 to 0.6 mm
Cartilage tissue regeneration was not found.
2) Distance of 0.7 to 1.3 mm (FIG. 9)
The gap provided on PAMPS/PAAm gel surface showed local cartilage tissue regeneration.
3) Distance of 1.4 to 2.0 mm (FIG. 10)
Cartilage regeneration tissue was scarcely found in the vicinity of a bone surface.
4) Distance of 2.1 to 2.8 mm (FIG. 11)
A tissue image, which was similar to steatosis-like necrosis, was found on PAMPS/PAAm gel surface, and a site in the vicinity of an articular surface showed chondroid tissue regeneration in parallel with the articular surface.
5) Distance of over 2.8 mm (FIG. 12)
A tissue image, which was similar to steatosis-like necrosis, was found on PAMPS/PAAm gel surface, and a site in the vicinity of an articular surface showed chondroid tissue regeneration in parallel with the articular surface.

Figure 17:
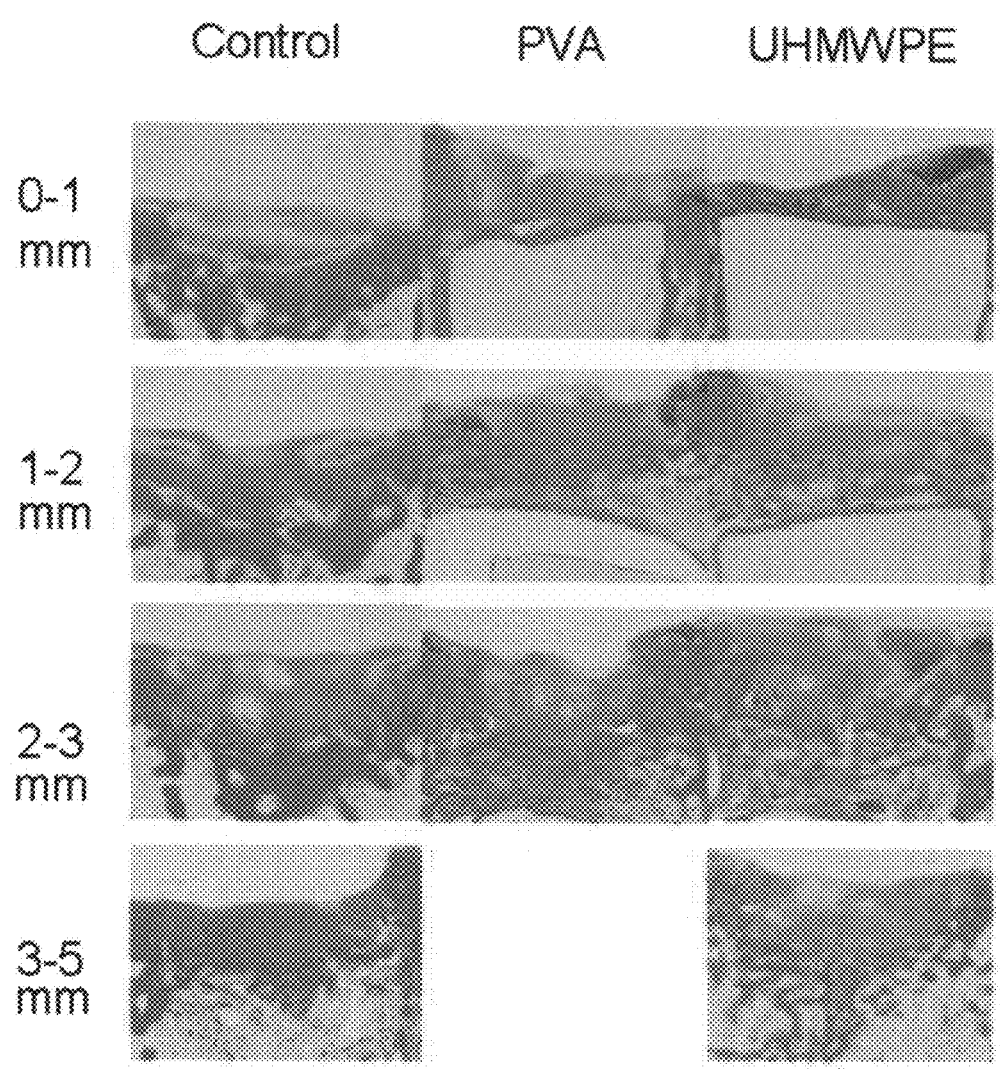
FIG. 17 shows histologic stained images (safranin-O stained image) for specimen in which control polyvinyl alcohol gel is filled in bone defect portion, and specimen in which UHMPE is filled in bone defect portion.

<Control>
Under the same conditions as Test 1, both specimen in which polyvinyl alcohol gel was filled in bone defect portion in lieu of the bone filler of this invention, and specimen in which Ultra High Molecular Weight polyethylene (UHMPE) used as an artificial joint material was filled in bone defect portion showed no cartilage tissue regeneration (FIG. 17).

The invention claimed is:

1. A method for inducing in vivo regeneration of a hyaline cartilage tissue and a subchondral bone tissue, comprising the steps of:
   (a) preparing a hydrogel having an interpenetrating network structure comprising
      (i) a polymer having a crosslinked network structure with 2-acrylamide-2-methylpropanesulfonic acid or 2-acrylamide-2-methylpropane sodium sulphate as a raw monomer and
      (ii) a polymer having a crosslinked network structure with N,N-dimethyl-acrylamide or acrylamide as a raw monomer;
   (b) forming a hole or groove in a subchondral bone below a damaged cartilage tissue; and
   (c) filling said hole or groove with said hydrogel, whereby the hydrogel promotes in vivo regeneration of a hyaline cartilage tissue and a subchondral bone tissue in the absence of transplantation of an autologous cartilage tissue or undifferentiated cells.

2. The method of claim 1, whereby said in vivo regeneration of a hyaline cartilage tissue and a subchondral bone tissue is promoted in the absence of transplantation of undifferentiated cells.

3. A method for inducing in vivo regeneration of a hyaline cartilage tissue and a subchondral bone tissue, comprising the steps of:
   (a) forming a hole or groove in a subchondral bone below a damaged cartilage tissue; and
   (b) filling said hole or groove with a hydrogel in an amount effective for inducing in vivo regeneration of a hyaline cartilage tissue and a subchondral bone tissue, wherein said hydrogel has an interpenetrating network structure comprising
      (i) a polymer having a crosslinked network structure with 2-acrylamide-2-methylpropanesulfonic acid or 2-acrylamide-2-methylpropane sodium sulphate as a raw monomer and
      (ii) a polymer having a crosslinked network structure with N,N-dimethyl-acrylamide or acrylamide as a raw monomer, and
   whereby the hydrogel promotes in vivo regeneration of a hyaline cartilage tissue and a subchondral bone tissue in the absence of transplantation of an autologous cartilage tissue or undifferentiated cells.

* * * * *